US00PP22959P2

(12) United States Plant Patent
Beekenkamp

(10) Patent No.: US PP22,959 P2
(45) Date of Patent: Aug. 14, 2012

(54) POINSETTIA PLANT NAMED 'BKPONTW'

(50) Latin Name: ***Euphorbia pulcherrima* Willd.**
Varietal Denomination: BKPONTW

(75) Inventor: Annie Cornelia Beekenkamp, Maasdijk (NL)

(73) Assignees: Agriom B.V., De Kwakel (NL); Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 12/932,729

(22) Filed: Mar. 4, 2011

(51) Int. Cl.
*A01H 5/00* (2006.01)

(52) U.S. Cl. ..... Plt./307

(58) Field of Classification Search ..... Plt./307
See application file for complete search history.

*Primary Examiner* — Kent L Bell

(74) *Attorney, Agent, or Firm* — C. A. Whealy

(57) ABSTRACT

A new and distinct cultivar of Poinsettia plant named 'BKPONTW', characterized by its compact and upright plant habit; vigorous growth habit; thick stems; twisting leaves; inflorescences with twisting red-colored flower bracts; and excellent post-production longevity.

2 Drawing Sheets

Botanical designation: *Euphorbia pulcherrima* Willd.
Cultivar denomination: 'BKPONTW'.

BACKGROUND OF THE INVENTION

The present invention relates to a new and distinct cultivar of Poinsettia plant, botanically known as *Euphorbia pulcherrima* Willd., and hereinafter referred to by the name 'BKPONTW'.

The new Poinsettia plant is a naturally-occurring whole plant mutation of *Euphorbia pulcherrima* Willd. 'Floasatur', disclosed in U.S. Plant Pat. No. 20,230. The new Poinsettia plant was discovered and selected by the Inventor in 2008 as a flowering plant from within a population of plants of 'Floasatur' in a controlled greenhouse environment in De Kwakel, The Netherlands.

Asexual reproduction of the new Poinsettia plant by terminal vegetative cuttings in a controlled greenhouse environment in Maasdijk, The Netherlands since 2009 has shown that the unique features of this new Poinsettia plant are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'BKPONTW'. These characteristics in combination distinguish 'BKPONTW' as a new and distinct cultivar of Poinsettia plant:

1. Compact and upright plant habit.
2. Vigorous growth habit.
3. Thick stems.
4. Twisting leaves.
5. Inflorescences with twisting red-colored flower bracts.
6. Excellent post-production longevity.

Plants of the new Poinsettia differ primarily from plants of the parent, 'Floasatur', in leaf and flower bract orientation as plants of 'Floasatur' have flat (not twisting) leaves and flower bracts.

Plants of the new Poinsettia can be compared to plants of *Euphorbia pulcherrima* Willd. 'Valentino', not patented. In side-by-side comparisons conducted in Maasdijk, The Netherlands, plants of the new Poinsettia differed primarily from plants of 'Valentino' in the following characteristics:

1. Plants of the new Poinsettia were more compact than plants of 'Valentino'.
2. Plants of the new Poinsettia and 'Valentino' differed in flower bract shape.

BRIEF DESCRIPTION OF THE PHOTOGRAPHS

The accompanying photographs illustrate the overall appearance of the new Poinsettia plant. The photographs show the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet comprises a side perspective view of a typical flowering plant of 'BKPONTW' grown in a container.

The photograph on the second sheet is a close-up view of a typical flowering plant of 'BKPONTW'.

DETAILED BOTANICAL DESCRIPTION

The aforementioned photographs and following observations and measurements describe plants grown during the winter in 13-cm containers in a glass-covered greenhouse in Maasdijk, The Netherlands and under conditions and practices which approximate those generally used in commercial Poinsettia production. During the first six weeks of production of the plants, day and night temperatures averaged 20° C.; after the first six weeks, temperatures were reduced to 17° C. until flowering. During the production period, light levels averaged 200 Watts per square meter. Measurements and numerical values represent averages for typical flowering plants. Plants were pinched one time and were 18 weeks old when the photographs and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'BKPONTW'.

Parentage:

Naturally-occurring whole plant mutation of *Euphorbia pulcherrima* Willd. 'Floasatur', disclosed in U.S. Plant Pat. No. 20,230.

Propagation:

*Type*.—Terminal vegetative cuttings.

*Time to initiate roots, summer*.—About 16 days at 20° C. to 23° C.

*Time to initiate roots, winter*.—About 17 days at 20° C. to 23° C.

*Time to produce a rooted young plant, summer*.—About four weeks at 20° C. to 23° C.

*Time to produce a rooted young plant, winter*.—About five weeks at 20° C. to 23° C.

*Root description*.—Medium in thickness, fibrous; white in color.

*Rooting habit*.—Moderately freely branching; medium density.

Plant description:

*Plant and growth habit*.—Compact and upright plant habit; inverted triangle with rounded crown; large inflorescences positioned above the foliar plane; vigorous growth habit.

*Plant height*.—About 25 cm.

*Plant diameter or spread*.—About 40 cm.

*Lateral branch description*.—Quantity: Moderately freely branching habit, about five lateral branches develop after pinching. Length: About 20 cm. Diameter: Thick, about 6 mm. Internode length: About 1 cm to 3 cm. Strength: Strong. Texture: Smooth, glabrous. Color: Close to 146A.

*Foliage description*.—Arrangement: Alternate, simple. Length: About 11 cm. Width: About 8 cm. Shape: Ovate. Apex: Acute. Base: Obtuse. Margin: Entire to parted. Venation pattern: Pinnate. Orientation: Twisting. Texture, upper and lower surfaces: Glabrous; slightly rugose. Color: Developing and fully developed leaves, upper surface: Close to 139A; venation, close to 187B. Developing and fully developed leaves, lower surface: Close to 189A; venation, close to 147B with a reddish blush. Petiole: Length: About 5 cm. Diameter: About 2 mm. Texture, upper and lower surfaces: Smooth, glabrous. Color, upper and lower surfaces: Close to 183B.

Inflorescence description:

*Inflorescence type and habit*.—Inflorescences are compound corymbs of cyathia with red-colored twisting flower bracts subtending the cyathia; one inflorescence per lateral branch with inflorescences positioned above and beyond the foliar plane.

*Fragrance*.—None detected.

*Natural flowering season*.—Plants flower naturally during the winter under long nyctoperiod conditions; inflorescence initiation and development can be induced under artificial long nyctoperiod conditions; early flowering habit, response time is about seven weeks.

*Post-production longevity*.—Excellent post-production longevity; plants of the new Poinsettia maintain good substance and bract color for about eight weeks under interior conditions.

*Inflorescence size*.—Diameter: About 20 cm. Height (depth): About 5 cm.

*Flower bracts*.—Quantity per inflorescence: About twelve. Length: About 10 cm. Width: About 6.5 cm. Shape: Ovate. Apex: Acuminate. Base: Obtuse. Margin: Entire. Venation: Pinnate. Orientation: Twisting. Texture, upper surface: Glabrous; slightly rugose. Color: Developing and transitional bracts, upper surface: Close to 187B. Developing and transitional bracts, lower surface: Close to 147B. Fully developed bracts, upper surface: Close to 53B. Fully developed bracts, lower surface: Close to 64C. Bract petiole: Length: About 2 cm. Diameter: About 2 mm. Texture, upper and lower surfaces: Smooth, glabrous. Color, upper and lower surfaces: Close to 187B.

*Cyathia*.—Quantity per corymb: About seven. Length: About 1 cm. Width: About 5 mm. Shape: Ovoid. Color, immature: Close to 144B. Color, mature: Close to 144A; towards the apex, close to 53B. Nectaries: Quantity per cyathium: One or two. Length: About 6 mm. Diameter: About 3 mm. Color: Immature, inner and outer surfaces: Close to 149C. Mature, inner surface: Close to 15C. Mature, outer surface: Close to 15C and 25B.

*Peduncles*.—Length: About 5 mm to 10 mm. Diameter: About 5 mm. Strength: Strong. Texture: Smooth, glabrous. Color: Close to 146A blushed with red.

*Reproductive organs*.—Stamens: Quantity per cyathium: About eight to ten. Filament length: About 3 mm. Filament color: Close to 45A. Anther shape: Oval. Anther length: About 0.5 mm. Anther color: Close to 6B. Amount of pollen: Abundant. Pollen color: Close to 9A. Pistils: Quantity per cyathium: One. Pistil length: About 3 mm. Style length: About 3 mm. Style color: Close to 46B. Stigma shape: Rounded to oval. Stigma color: Close to 46B. Ovary color: Close to 144A. Seeds and fruits: Seed and fruit production has not been observed on plants of the new Poinsettia.

Disease/pest resistance: Plants of the new Poinsettia have not been shown to be resistant to pathogens and pests common to Poinsettia plants.

Temperature tolerance: Plants of the new Poinsettia have been observed to tolerate temperatures ranging from about 12° C. to about 25° C.

It is claimed:

1. A new and distinct Poinsettia plant named 'BKPONTW' as illustrated and described.

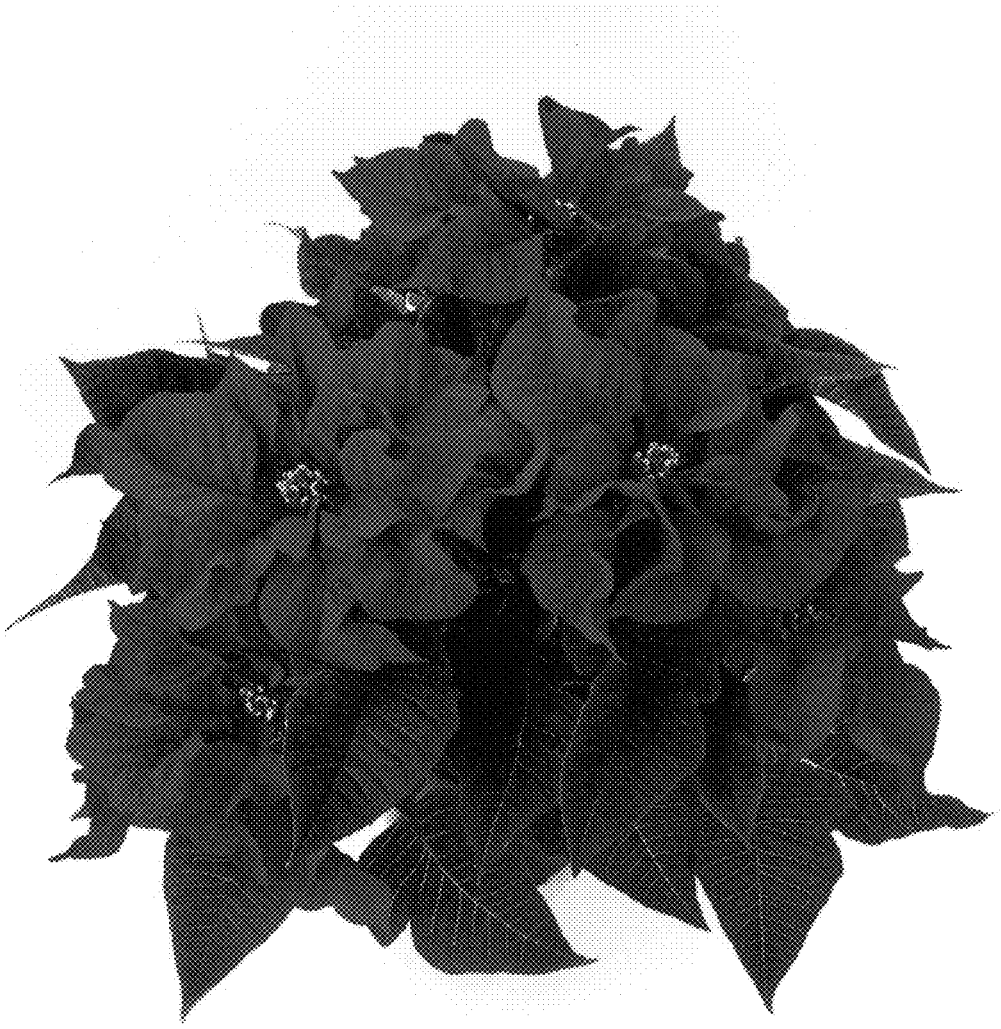

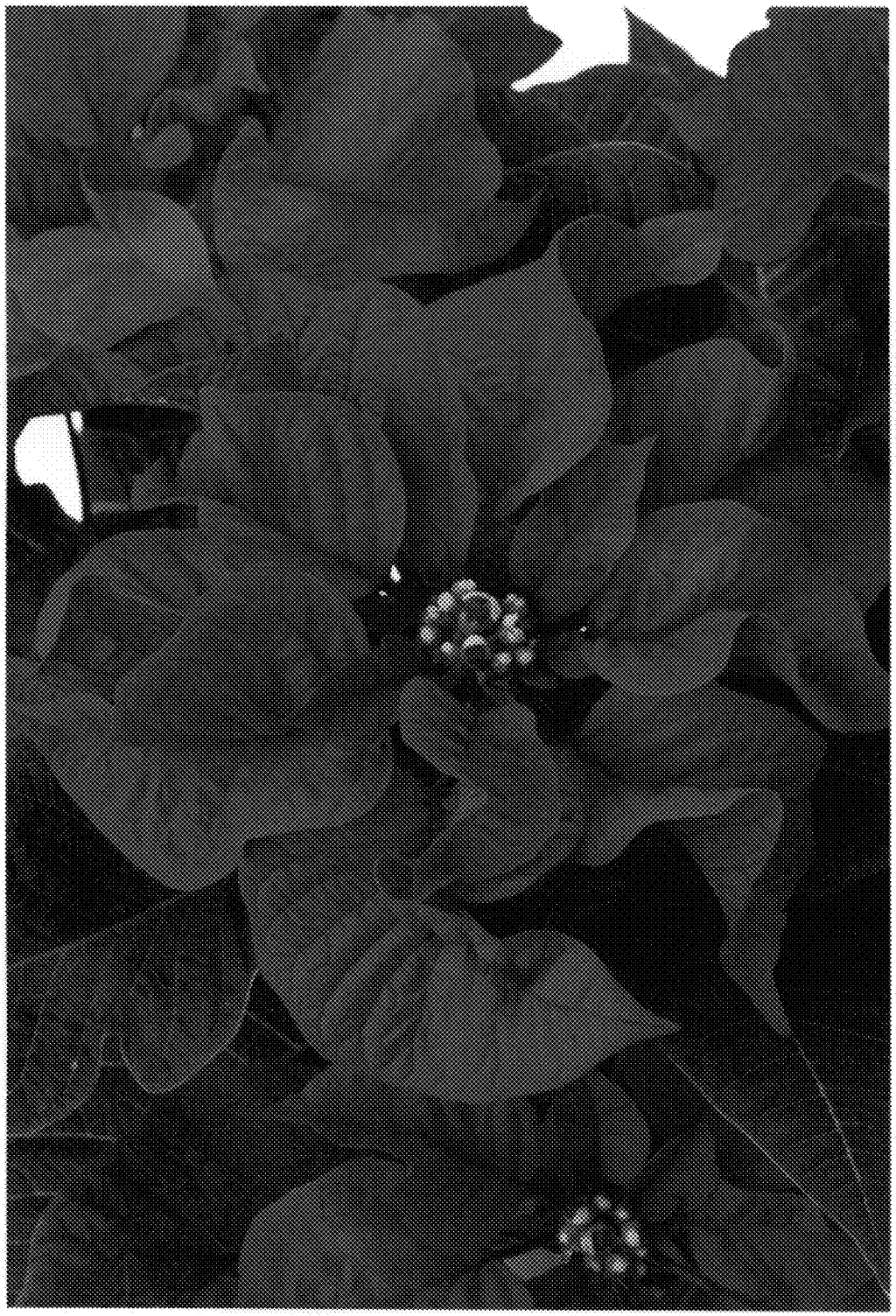

* * * * *